(12) United States Patent
Xu

(10) Patent No.: US 10,736,873 B2
(45) Date of Patent: Aug. 11, 2020

(54) MEDICAL USES OF N-(2-AMINOETHYL)-N-(4-BENZYLOXY)-3-METHOXYBENZYL)THIOPHENE-2-FORMAMIDE HYDROCHLORIDE

(71) Applicant: The Second Xiangya Hospital, Central South University, Changsha, Hunan (CN)

(72) Inventor: Xundi Xu, Hunan (CN)

(73) Assignee: The Second Xiangya Hospital, Central South University (CN)

( * ) Notice: Subject to any disclaimer, the term of this patent is extended or adjusted under 35 U.S.C. 154(b) by 0 days.

(21) Appl. No.: 16/490,308

(22) PCT Filed: Mar. 8, 2017

(86) PCT No.: PCT/CN2017/075943
§ 371 (c)(1),
(2) Date: Aug. 30, 2019

(87) PCT Pub. No.: WO2018/161271
PCT Pub. Date: Sep. 13, 2018

(65) Prior Publication Data
US 2020/0000769 A1    Jan. 2, 2020

(51) Int. Cl.
| | | |
|---|---|---|
| *A61K 31/381* | (2006.01) |
| *A61P 35/00* | (2006.01) |
| *A61K 9/00* | (2006.01) |
| *A61K 31/404* | (2006.01) |
| *A61K 31/44* | (2006.01) |

(52) U.S. Cl.
CPC .......... *A61K 31/381* (2013.01); *A61K 9/0019* (2013.01); *A61P 35/00* (2018.01); *A61K 31/404* (2013.01); *A61K 31/44* (2013.01)

(58) Field of Classification Search
CPC .................................................. A61K 31/381
See application file for complete search history.

(56) References Cited

PUBLICATIONS

Liu, Expression of TRPM8 in primary hepatocellular carcinoma and its clinical significance, Medicine & Public Health, China Master's Thesis, No. 2, Feb. 8, 2012.*
Almeida et al., Pharmacological blockade of the cold receptor TRPM8 attenuates autonomic and behavioral cold defenses and decreases deep body temperature, Journal of Neuroscience (2012), 32(6), 2086-2099.*
Almeida, M.C. et al., "Pharmacological Blockade of the Cold Receptor TRPM8 Attenuates Autonomic and Behavioral Cold Defenses and Decreases Deep Body Temperature", The Journal of Neuroscience, 32(6), Feb. 8, 2012, pp. 2086-2099.
Liu, Jiefeng, "Expression of TRPM8 in Primary Hepatocellular Carcinoma and its Clinical Significance", Medicine & Public Health, China Master's Theses, No. 2, Feb. 8, 2012.
International Search Report for PCT/CN2017/075943, dated Nov. 29, 2017.

* cited by examiner

*Primary Examiner* — Svetlana M Ivanova
(74) *Attorney, Agent, or Firm* — Lerner, David, Littenberg, Krumholz & Mentlik, LLP

(57) ABSTRACT

The present invention relates to the use of N-(2-aminoethyl)-N-(4-benzyloxy)-3-methoxybenzyl)thiophene-2-formamide hydrochloride for treating liver cancer. The N-(2-aminoethyl)-N-(4-benzyloxy)-3-methoxybenzyl)thiophene-2-formamide hydrochloride of the present invention can effectively inhibit the growth of liver cancer cells and has a therapeutic effect on liver cancer.

19 Claims, 1 Drawing Sheet

Days after treatment with medicament(HepG2)

Weeks after treatment with medicament (HUH7)

MEDICAL USES OF N-(2-AMINOETHYL)-N-(4-BENZYLOXY)-3-METHOXYBENZYL)THIOPHENE-2-FORMAMIDE HYDROCHLORIDE

CROSS REFERENCE TO RELATED APPLICATIONS

The present application is a national phase entry under 35 U.S.C. § 371 of International Application No. PCT/CN2017/075943, filed Mar. 8, 2017, of which is hereby incorporated herein by reference.

TECHNICAL FIELD

The present invention relates to the field of pharmacy. Specifically, the present invention relates to the use of N-(2-aminoethyl)-N-(4-benzyloxy)-3-methoxybenzyl)thiophene-2-formamide hydrochloride for preparing a medicament for treating liver cancer.

BACKGROUND OF ART

Primary liver cancer is one of top ten malignant tumors published by the World Health Organization, and its incidence rates in men and in women rank fifth and seventh in the world respectively, ranking third among the deadly diseases caused by cancer. The new and dead cases of each year in the world account for 5.4% of all malignant tumors. In the United States, the incidence rate of primary liver cancer caused by hepatitis C infections has increased year by year. Chronic hepatitis B virus infection, hepatitis C virus infection, alcoholic liver disease, nonalcoholic fatty liver and metabolic related diseases(hemochromatosis) etc., can all lead to the occurrence of liver cancer. About 85% of liver cancer patients develop from progressive liver fibrosis and/or hepatic cirrhosis. Hepatitis B remains the leading cause of cancer in the world. China is a big country with liver diseases. According to statistics, there are more than 100 million people with liver diseases, that is, there is one liver disease patient in every ten people. Among them the most prominent liver disease is the liver cancer which is further evolved from hepatic cirrhosis caused by hepatitis B virus infection. According to the analysis of the global cancer statistics in 2005 from the World Health Organization, currently, the number of new cases of liver cancer in each year is 626,000, and the number of death is 598,000. It is estimated that in the world, 2 billion people suffer from hepatitis B and 200 million people suffer from hepatitis C. Meanwhile, it is also expected that primary liver cancer will become the second cancer-causing deadly disease by 2030. 55% of new patients with liver cancer are from China.

At present, with the development and advancement of medicine, the therapeutic effect of primary liver cancer has been improved to some extent, and the five-year survival rate has reached 40-70%. Comprehensive treatment has become a basic principle of liver cancer treatment, including surgical hepatectomy and liver transplantation, interventional therapy including radiofrequency ablation, microwave therapy and transarterial chemoembolization therapy, etc. Some targeted medicaments have been applied clinically, such as Sorafenib, Sunitinib and so on. However, because of the high invasiveness and high recurrence rate of primary liver cancer, it still seriously affects the therapeutic effect of such patients. Chemotherapy regimens, especially the discovery of new targeting therapeutic drugs, are expected to provide new ways and means for the treatment of liver cancer.

The transient receptor potential (TRP) channel is an important class of cation channel superfamily located on the cell membrane. TRP channels are widely distributed and have different regulatory mechanisms. By sensing various stimuli inside and outside the cell, they participate in many life activities such as algesia, mechanical sensation, genesis of gustatory, maintaining ionic homeostasis in the internal and external environment of cell and so on, having the functions of regulating muscle contraction, transmitter release, cell proliferation, cell differentiation, gene transcription, cell apoptosis and cell death, etc. The TRP channel subtype TRPM8 is a non-selective cation channel which was originally cloned as a prostate-specific protein. At present, TRPM8 has been found to be expressed in pancreatic cancer, colon cancer, lung cancer, breast cancer, prostate cancer, bladder cancer, oral cancer, neuroendocrine tumor, and skin-derived malignant tumor. TRPM8 can be stimulated by cold and activated by menthol. TRPM8 is involved in the regulation of thermesthesia and pain sensation, and can regulate expansion and contraction of blood vessels, especially playing an important role in terms of regulating cell growth and death. Preliminary studies have shown that TRPM8 can play a role by regulating the reproduction and invasion-metastasis ability of tumor cells. Therefore, inhibition of TRPM8 can reduce the incidence of colorectal cancer.

N-(2-aminoethyl)-N-(4-benzyloxy)-3-methoxybenzyl) thiophene-2-formamide hydrochloride (also known as: M8-B hydrochloride, molecular formula: $C_{22}H_{24}N_2O_3S \cdot HCl$) has the structural formula I shown below, which can be prepared according to the method of Example 3-1 of International Patent Publication WO2006/040136.

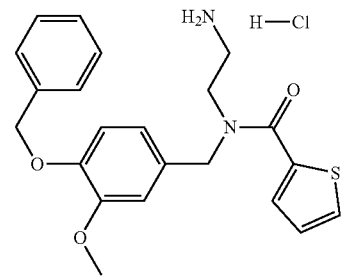

It remains to be further studied that N-(2-aminoethyl)-N-(4-benzyloxy)-3-methoxybenzyl)thiophene-2-formamide hydrochloride causes biological function changes by blocking TRPM8.

SUMMARY OF THE INVENTION

The present inventors have found that N-(2-aminoethyl)-N-(4-benzyloxy)-3-methoxybenzyl)thiophene-2-formamide hydrochloride has a therapeutic effect on liver cancer.

Therefore, the purpose of the present invention is to provide the use of N-(2-aminoethyl)-N-(4-benzyloxy)-3-methoxybenzyl)thiophene-2-formamide hydrochloride in the preparation of a medicament for treating liver cancer. Said medicament further comprises one or more pharmaceutically acceptable adjuvant(s).

The medicament of the present invention comprising N-(2-aminoethyl)-N-(4-benzyloxy)-3-methoxybenzyl)thiophene-2-formamide hydrochloride is used for treating liver cancer.

Multi-factor, multi-stage, multi-gene and multi-signal pathway transduction are involved in tumorigenesis. Therefore, the combination of anti-tumor medicaments with different mechanisms of action is expected to improve the therapeutic effect.

In a preferred embodiment of the present invention, the medicament of the present invention is also used in combination with at least one additional medicament for treating liver cancer. Wherein said additional medicament is selected from Sorafenib, Sunitinib, or a combination thereof, preferably, Sorafenib.

The medicament or pharmaceutical composition prepared from the above compound of the formula I of the present invention can be administrated in a common way such as oral administration, injection administration (e.g. intramuscular injection, intravenous injection, intraperitoneal injection), subcutaneous administration, inhalation administration, rectal administration and so on, and can be prepared in a common formulation, such as tablet, capsule, suppository, powder for injection, injection, aerosol and so on.

In a preferred embodiment of the present invention, the compound with the structure shown above in formula I of the present invention is administered in a way of injection administration, calculated according to a person's weight (kg), preferably at a dose of 2 mg/kg, administered in a way of intraperitoneal injection with a dosing frequency of 1 time/day. For an animal, the dose is 2 mg/kg, the way of administration is intraperitoneal injection with a dosing frequency of 1 time/day.

EMBODIMENT

Figure 1:
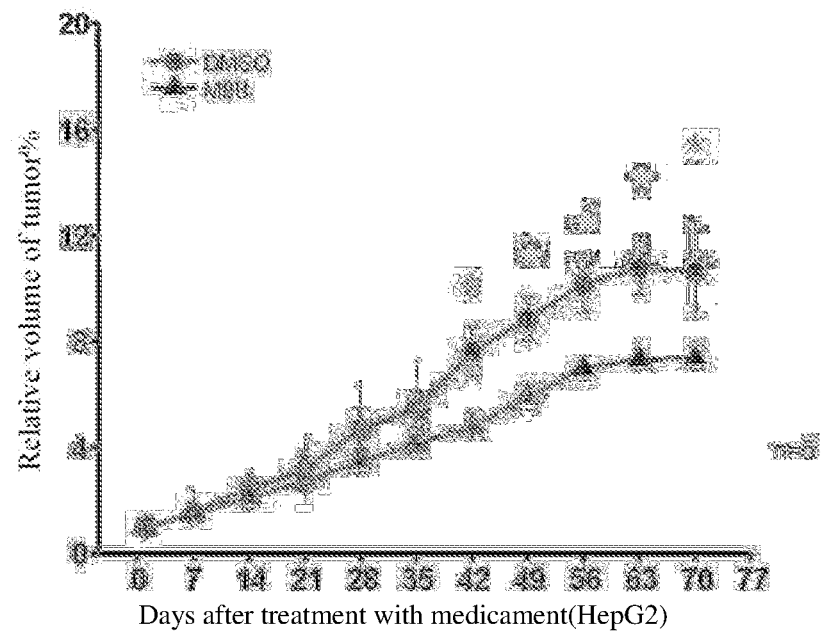
FIG. 1 shows the relative volume of Scid-HepG2-subcutaneous tumor of the control group and the therapeutic intervention group of Example 1.
Figure 2:
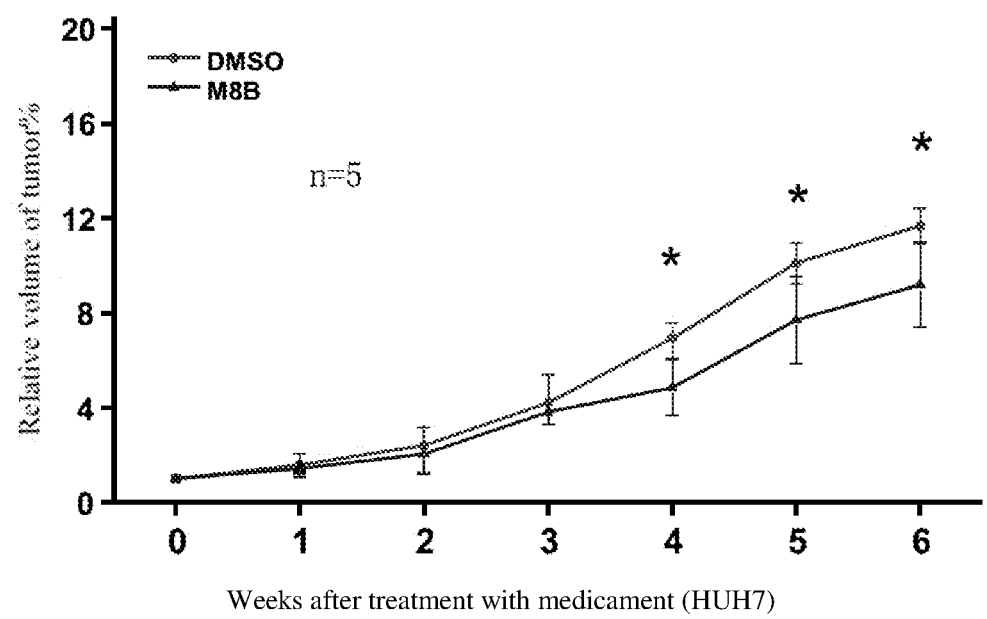
FIG. 2 shows the relative volume of Scid-Huh7-subcutaneous tumor of the control group and the therapeutic intervention group of Example 2.

The technical solutions of the present invention are further described in detail below in combination with specific examples. It should be appreciated that these examples are intended to illustrate the basic principles, main features and advantages of the present invention, and the specific implementation conditions employed in the examples may be appropriately adjusted within the scope of the art, and the protection scope of the present invention is not limited by the examples.

In examples of the present invention, the following materials were used:

4-week-old female non-obese diabetic/severe combined immunodeficiency (NOD/SCID) nude mice, purchased from Beijing Vital River Company;

Hepatoma cell lines HepG2 and Huh7, purchased from the Cell Bank of the Shanghai Institute of Life Sciences, Chinese Academy of Sciences;

M8-B hydrochloride injectable medication was purchased from Sigma Aldrich Company and the article number of this reagent was SML0893, which was dissolved in DMSO.

Statistical method: t-test

EXAMPLES

Example 1

Using the hepatoma cell line HepG2, $5\times10^6$ cells were injected into the right flank of each NOD/SCID nude mouse (10 in total) respectively. When the tumor grows to a volume of about 80 mm$^3$, the mice were randomly divided into control group and therapeutic intervention group, with 5 mice in each group.

Therapeutic Intervention Group:

M8-B hydrochloride was dissolved in DMSO to form an injectable medication, intraperitoneally injected, at a dose of 2 mg/kg (wherein 2 mg was the mass of M8-B hydrochloride), 1 time/day.

Control Group:

The blank solvent DMSO was intraperitoneally injected, at a dose of 2 mg/kg, 1 time/day.

Tumor size was measured by volume=½×length×width$^2$, and the mice were sacrificed at week 10 to compare survival rate and tumor volume. The experimental results of this example are as follows:

Tumor size was measured by volume=½×length×width$^2$, and mice were sacrificed at week 10 to compare survival rate and tumor volume. The experimental results of this example are as follows:

TABLE 1

Relative volumes of Scid-HepG2-subcutaneous tumors in control group and therapeutic intervention group.

| group | week number | | | | | |
|---|---|---|---|---|---|---|
| | 0 | 1 | 2 | 3 | 4 | 5 |
| DMSO | 100.00% | 157.32% | 243.49% | 318.54% | 4693.7% | 545.25% |
| M8B | 100.00% | 151.94% | 212.44% | 273.9% | 349.0% | 416.66% |
| P value | N.S | N.S | N.S | N.S | N.S | N.S. |

| group | week number | | | | |
|---|---|---|---|---|---|
| | 6 | 7 | 8 | 9 | 10 |
| DMSO | 764.32% | 885.24% | 1715.08% | 1013.89% | 1077.34% |
| M8B | 479.2% | 590.68% | 1108.50% | 700.92% | 734.87% |
| P value | 0.047 | 0.042 | 0.048 | 0.047 | 0.047 |

In Table 1, DMSO represents the relative volume of Scid-HepG2-subcutaneous tumor in the control group of blank solvent, M8-B represents the relative volume of Scid-HepG2-subcutaneous tumor in the therapeutic intervention group, and P value represents the difference between the relative volumes of Scid-HepG2-subcutaneous tumors in the control group and therapeutic intervention group. The tumor size on the first day of administration is 100%.

Example 2

Using the hepatoma cell line Huh7, $5×10^6$ cells were injected into the right flank of each NOD/SCID nude mouse (10 in total) respectively. When the tumor grows to a volume of about 80 $mm^3$, the mice were randomly divided into control group and therapeutic intervention group, with 5 mice in each group.

Therapeutic Intervention Group:

M8-B hydrochloride was dissolved in DMSO to form an injectable medication, intraperitoneally injected, at a dose of 2 mg/kg (wherein 2 mg was the mass of M8-B hydrochloride), 1 time/day.

Control Group:

The blank solvent DMSO was intraperitoneally injected, at a dose of 2 mg/kg, 1 time/day.

Tumor size was measured by volume=½×length×$width^2$, and the mice were sacrificed at week 6 to compare survival rate and tumor volume. The experimental results of this example are as follows:

TABLE 2

Relative volumes of Scid-Huh7-subcutaneous tumors in control group and therapeutic intervention group.

| group | week number | | | |
|---|---|---|---|---|
| | 0 | 1 | 2 | 3 |
| DMSO | 100.00% | 157.56% | 239.44% | 421.0% |
| M8B | 100.00% | 143.85% | 205.0% | 381.41% |
| P value | N.S | N.S | N.S | N.S |

| group | week number | | |
|---|---|---|---|
| | 4 | 5 | 6 |
| DMSO | 692.88% | 1010.21% | 1167.05% |
| M8B | 484.0% | 789.89% | 928.01% |
| P value | 0.04 | 0.038 | 0.009 |

In Table 2, DMSO represents the relative volume of Scid-Huh7-subcutaneous tumor in the control group of blank solvent, M8-B represents the relative volume of Scid-Huh7-subcutaneous tumor in the therapeutic intervention group, and P value represents the difference between the relative volumes of Scid-Huh7-subcutaneous tumors in the control group and therapeutic intervention group. The tumor size on the first day of administration is 100%.

As can be seen from the results of tables 1 and 2, the changes of tumor volume in mice injected with N-(2-aminoethyl)-N-(4-benzyloxy)-3-methoxybenzyl)thiophene-2-formamide hydrochloride are significantly slower, indicating that N-(2-aminoethyl)-N-(4-benzyloxy)-3-methoxybenzyl)thiophene-2-formamide hydrochloride has therapeutic effects on HepG2 and HuH7 tumors.

The invention claimed is:

1. A method of treating liver cancer, comprising administering an effective amount of a medicament comprising N-(2-aminoethyl)-N-(4-benzyloxy)-3-methoxybenzyl)thiophene-2-formamide hydrochloride to a human with liver cancer.

2. The method according to claim 1, wherein said medicament further comprises one or more pharmaceutically acceptable adjuvant(s).

3. The method according to claim 1, wherein said medicament is used in combination with at least one additional medicament for treating liver cancer.

4. The method according to claim 3, wherein said additional medicament is selected from Sorafenib, Sunitinib, or a combination thereof.

5. The method according to claim 4, wherein said additional medicament is Sorafenib.

6. The method according to claim 1, wherein said medicament is administered in ways comprising: oral administration, injection administration, subcutaneous administration, inhalation administration, rectal administration.

7. The method according to claim 6, wherein said injection administration is selected from intramuscular injection, intravenous injection or intraperitoneal injection.

8. The method according to claim 1, wherein said medicament is prepared as a tablet, a capsule, a suppository, a powder for injection, an injection or an aerosol.

9. The method according to claim 2, wherein said medicament is used in combination with at least one additional medicament for treating liver cancer.

10. The method according to claim 9, wherein said additional medicament is selected from Sorafenib, Sunitinib, or a combination thereof.

11. The method according to claim 10, wherein said additional medicament is Sorafenib.

12. The method according to claim 2, wherein said medicament is administered in ways comprising: oral administration, injection administration, subcutaneous administration, inhalation administration, rectal administration.

13. The method according to claim 3, wherein said medicament is administered in ways comprising: oral administration, injection administration, subcutaneous administration, inhalation administration, rectal administration.

14. The method according to claim 9, wherein said medicament is administered in ways comprising: oral administration, injection administration, subcutaneous administration, inhalation administration, rectal administration.

15. The method according to claim 4, wherein said medicament is administered in ways comprising: oral administration, injection administration, subcutaneous administration, inhalation administration, rectal administration.

16. The method according to claim 10, wherein said medicament is administered in ways comprising: oral administration, injection administration, subcutaneous administration, inhalation administration, rectal administration.

17. The method according to claim 5, wherein said medicament is administered in ways comprising: oral administration, injection administration, subcutaneous administration, inhalation administration, rectal administration.

18. The method according to claim 11, wherein said medicament is administered in ways comprising: oral administration, injection administration, subcutaneous administration, inhalation administration, rectal administration.

19. The method according to claim 12, wherein said injection administration is selected from intramuscular injection, intravenous injection or intraperitoneal injection.

* * * * *